(12) United States Patent
Okanojo et al.

(10) Patent No.: US 9,290,789 B2
(45) Date of Patent: Mar. 22, 2016

(54) METHOD FOR MEASURING CELLS, AND REAGENT FOR CELL MEASUREMENT

(71) Applicant: HITACHI HIGH-TECHNOLOGIES CORPORATION, Tokyo (JP)

(72) Inventors: Masahiro Okanojo, Tokyo (JP); Hideyuki Noda, Tokyo (JP); Shinichi Fukuzono, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/362,645

(22) PCT Filed: Nov. 28, 2012

(86) PCT No.: PCT/JP2012/080760
§ 371 (c)(1),
(2) Date: Jun. 4, 2014

(87) PCT Pub. No.: WO2013/084772
PCT Pub. Date: Jun. 13, 2013

(65) Prior Publication Data
US 2014/0342386 A1    Nov. 20, 2014

(30) Foreign Application Priority Data
Dec. 5, 2011  (JP) .................. 2011-265728

(51) Int. Cl.
C12Q 1/06      (2006.01)
C12Q 1/04      (2006.01)
C12Q 1/42      (2006.01)
G01N 21/76     (2006.01)
C12Q 1/34      (2006.01)

(52) U.S. Cl.
CPC .. *C12Q 1/06* (2013.01); *C12Q 1/04* (2013.01); *C12Q 1/34* (2013.01); *C12Q 1/42* (2013.01); *G01N 21/76* (2013.01)

(58) Field of Classification Search
None
See application file for complete search history.

(56) References Cited

U.S. PATENT DOCUMENTS 5,891,702 A      4/1999  Sakakibara et al.
2004/0009473 A1*  1/2004  Pease .............. C12Q 1/66
                                              435/5

FOREIGN PATENT DOCUMENTS

EP    0612850 A2    8/1994
EP    1134291 A1    9/2001
(Continued)

OTHER PUBLICATIONS

Hofmann "The contribution of coloured Maillard reaction products to the total colour of browned glucose/L-alanine solutions and studies on their formation" Z Lebensm Unters Forsch A (1999) 208: 17-26.*

(Continued)

*Primary Examiner* — Robert Yamasaki
*Assistant Examiner* — Charles Zoltan Constantine
(74) *Attorney, Agent, or Firm* — Mattingly & Malur, PC (57) ABSTRACT

A method and a means are provided, by which multiple types of cells can be simultaneously measured with high sensitivity by an ATP luminescence method. A method for measuring cells in a sample is provided, which comprises the steps of adding methanol to a sample suspected of containing viable cells to increase ATP within viable cells, extracting intracellular ATP, and causing extracted ATP to emit luminescence.

12 Claims, 5 Drawing Sheets

(56) References Cited

FOREIGN PATENT DOCUMENTS

| | | | |
|---|---|---|---|
| JP | 11-056393 | A | 3/1999 |
| JP | 11-253195 | A | 9/1999 |
| JP | 2000-189197 | A | 7/2000 |
| JP | 2004-511497 | A | 4/2004 |
| JP | 3547882 | B2 | 4/2004 |
| JP | 2006-081506 | A | 3/2006 |
| JP | 3811616 | B2 | 6/2006 |
| JP | 2006-174751 | A | 7/2006 |
| JP | 2006-246792 | A | 9/2006 |
| WO | 00/71675 | A1 | 11/2000 |
| WO | 02/32225 | A2 | 4/2002 |

OTHER PUBLICATIONS

Forman ("The Effect of Different Solvents on the ATP/ADP Content and Growth Properties of HeLa Cells" Journal Biochemical and Molecular Toxicology, 1999, vol. 13, No. 1).*

Hattori et al., "Enhanced microbial biomass assay using mutant luciferase resistant to benzalkonium chloride", Analytical Biochemistry, 2003, pp. 287-295, vol. 319.

Extended European Search Report received in corresponding European Application No. 12855701.4 dated Jun. 1, 2015.

Blaut, M. et al., "Coupling of ATP synthesis and methane formation from methanol and molecular hydrogen in Methanosarcina barkeri", European Journal of Biochemistry, 1984, p. 217-222, vol. 141, Germany.

* cited by examiner

METHOD FOR MEASURING CELLS, AND REAGENT FOR CELL MEASUREMENT

BACKGROUND OF THE INVENTION

1. Field of the Invention

The present invention relates to a method and a reagent for measuring cell counts or the presence of cells with high sensitivity by measuring intracellular ATP. In particular, the present invention relates to a method and a reagent for measuring cells (particularly viable cells) in a sample.

2. Background Art

Methods for measuring cell counts are employed in a broad range of fields, including the pharmaceutical, medical, food, brewing, and water treatment fields. In particular, in various fields such as pharmaceutical manufacturing, cosmetics manufacturing, clinical medicine, and basic biochemical fields, the presence or the absence of cells in samples is determined and cell counts are measured for the quality control of samples. For example, it is essential in the pharmaceutical manufacturing field to control microorganisms (bacteria and fungi) contained in pharmaceutical raw materials, pharmaceutical intermediates, final pharmaceutical products, and pharmaceutical water according to the Japanese Pharmacopoeia as standards stipulated by the Ministry of Health, Labour and Welfare. The number of microorganisms is measured daily.

Bacterial or fungal counts are mainly measured by a culture method as specified in the Japanese Pharmacopoeia. Such culture method involves bringing a sample into contact with an agar plate medium for culture, and then quantifying the number of colonies (CFU: Colony Forming Unit) as the number of microorganisms (microbial count) in the sample, with the use of the fact that one microorganism forms one colony as a result of culture.

Culture methods in the pharmaceutical industry have a problem that these methods require about 1 week for culture. Manufacturing is delayed at the intermediate production and final product shipping stages to wait for measurement results. Thus, such culture methods create temporal and economic burdens on the industry. In addition, culture methods necessitate choosing a specific medium types for each microbial species. A medium having a nutrient appropriate for the colony formation of each microorganism must be selected (Non-patent Document 1). For example, a standard agar medium is selected for general aerobic bacteria, R2A medium is selected for oligotrophic bacteria, a thioglycol medium is selected for anaerobic bacteria, and PDA medium is selected for fungi.

Specifically, aerobic bacteria are cultured in a standard agar medium at temperatures ranging from 30° C. to 35° C. for 48 to 72 hours, anaerobic bacteria are cultured in a thioglycolic acid medium at temperatures ranging from 30° C. to 35° C. for 5 or more days, oligotrophic bacteria are cultured in R2A medium at temperatures ranging from 20° C. to 25° C. (or 30° C. to 35° C.) for 4 to 7 days, and fungi are cultured in PDA medium at temperatures ranging from 20° C. to 25° C. for 5 or more days, for example. Hence, a plurality of protocols varying in medium, temperature, time for culture, and others appropriate for the colony formation of each microbial species are required. Accordingly, a single sample may need to be subdivided into a plurality of samples, or a plurality of samples may be required. Another problem is that a maximum of 7 days of culture is required for colony formation. Therefore, it has been difficult to measure the microbial counts of all microbial species using only one sample. Thus, measurement using a plurality of samples and a plurality of media has been essential.

An ATP (Adenosine TriPhosphate) luminescence method has been known as a method to rapidly measure cell counts with a shortened time of measurement. ATP to be measured is an organic compound that is contained within cells of all organisms and serves as an energy source required by cells' biological activity. The ATP luminescence method involves, with the use of luciferase and luciferin that chemically react with ATP to emit luminescence, measuring luminescence generated by a reaction of intracellular ATP with luciferase and luciferin, and thus estimating the cell count based on the luminescence level.

It has been generally known that when the ATP luminescence method is applied for cell counting, accurate viable cell counts cannot be estimated by directly measuring a sample, since ATP from viable cells (living microorganisms or live cells), ATP from dead cells (dead microorganisms), and free ATP are mixed within the single sample. To address this problem, an ATP elimination method using adenosine-phosphate deaminase, apyrase, and others in combination has been known (Patent Document 1).

According to a conventional intracellular ATP measurement method 101 (for measuring ATP within viable cells) (FIG. 1), a sample 102 containing viable-cell-derived ATP, dead-cell-derived ATP, and free ATP is subjected to three stages: (1) extracellular ATP removal 103 (for removing ATP outside of viable cells); (2) intracellular ATP extraction 104 (for extracting ATP within viable cells); and (3) the luminescent reaction of viable-cell-derived ATP with a luminescent reagent (e.g., luciferase and luciferin) and luminescence measurement 105. Therefore, the viable cell count is estimated based on luminescence resulting from the luminescent reaction of ATP within viable cells with the luminescent reagents.

Figure 1:
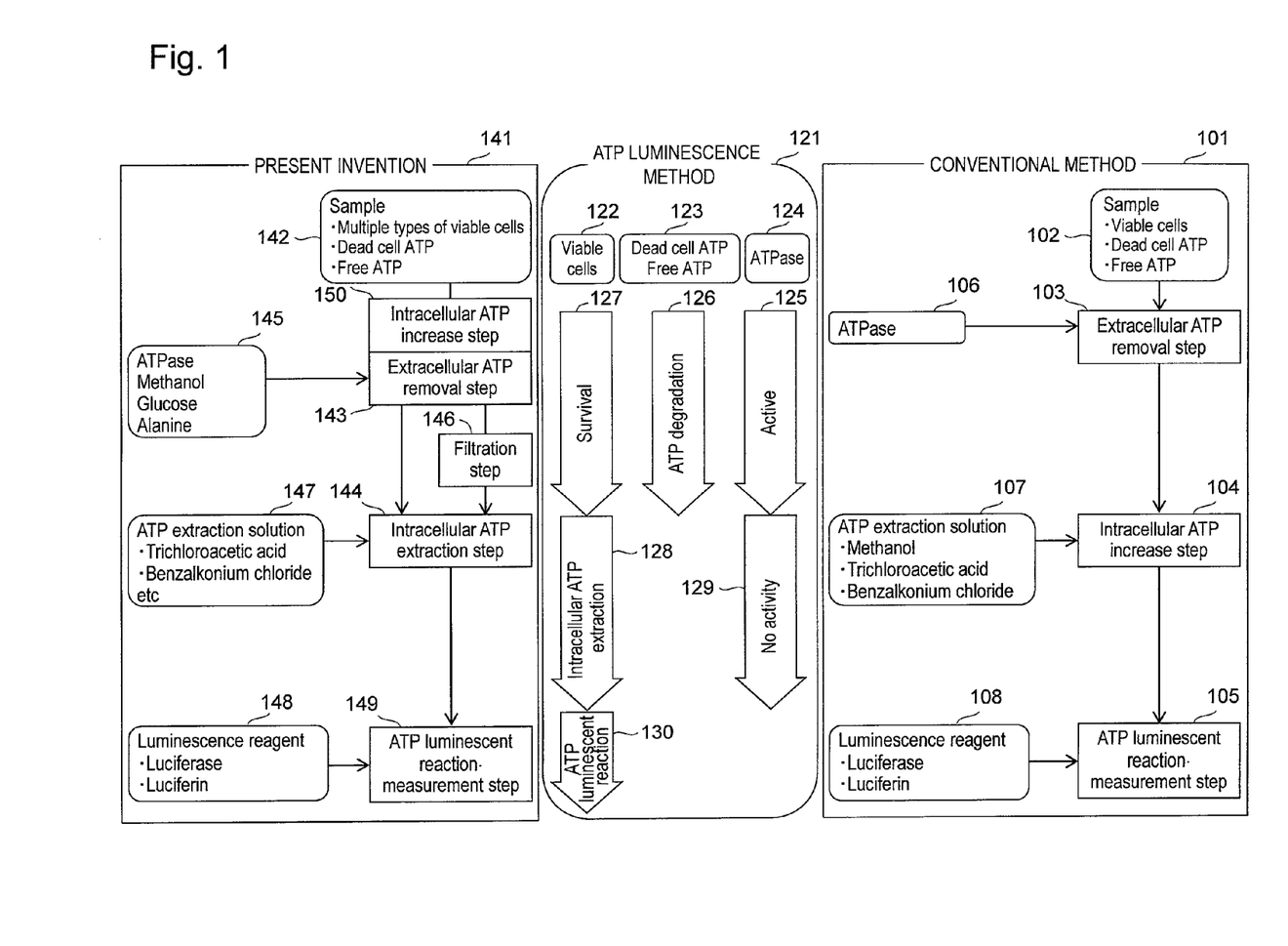
FIG. 1 shows the results of comparing the steps of the intracellular ATP luminescence method according to the present invention with the steps of a conventional ATP luminescence method for the states of ATP within viable cells, ATP within dead cells, free ATP, and ATPase.

The states of viable-cell-derived ATP 122, dead-cell-derived ATP, free ATP 123, and ATPase 124 in each step of the conventional intracellular ATP measurement method 101 (for measuring ATP within viable cells) and an ATP luminescence method 121 are as explained below.

In the extracellular ATP removal step 103 (for removing ATP outside of viable cells), dead-cell-derived ATP and free ATP 123 are mainly removed. In the removal method, ATPase 124 (e.g., apyrase) is added to a sample (106). Cell walls or cell membranes in dead cells are disrupted, therefore, ATP within dead cells and free ATP 123 are degraded by the activity 125 of ATPase 124 (126). On the other hand, viable cells 122 are living 127, and thus ATP within viable cells is isolated from ATPase 124 because of viable cells' walls or membranes (Patent Document 2). Patent Document 2 discloses that ATP within viable cells such as *Escherichia coli, Lactobacillus brevis, Staphyllococcus aureus*, and *Bacillus subtilis* can be increased following culture in standard media by adding glucose. Moreover, Patent Document 3 discloses that spore germination can be induced by adding glucose and alanine to spores.

In the intracellular ATP extraction step 104 (for extracting ATP within viable cells), "disruption of viable cells' walls" and "inactivation of ATPase" are performed. An ATP extraction method is performed by adding an ATP extraction solution 107 of trichloroacetic acid, benzalkonium chloride, methanol or the like (Patent Document 2). In the ATP extraction step 104, viable cells' walls are disrupted by such an additive, viable cells die, and thus ATP is extracted (128). On the other hand, ATPase loses its activity (129) due to the effect of enzyme denaturation by the additive, so as to preserve and protect ATP from degradation even after ATP is extracted from viable cells.

In the luminescent reaction of ATP with a luminescent reagent and luminescence measurement step 105, the thus extracted viable-cell-derived ATP is brought into contact with a luminescent reagent 108, so that a luminescent reaction 130 takes place. The thus generated luminescence is quantified using a luminescence measurement apparatus such as a luminometer. The luminescence level is proportional to the viable-cell-derived ATP count, and the ATP count is proportional to the viable cell count. Hence, the viable cell count can be estimated from the luminescence level. In addition, these 3 steps (the extracellular ATP removal step 103 (for removing ATP outside of viable cells), the intracellular ATP extraction step 104, and the ATP luminescent reaction•measurement step 105) proceed irreversibly.

The intracellular ATP level per viable cell is about $1.5 \times 10^{-18}$ mol/CFU (0.001 fmol/CFU=1 amol/CFU) in terms of 1 bacterial CFU (Non-patent Document 1). The sensitivity of ATP measurement using a general ATP luminescence method ranges from $1 \times 10^{-15}$ to $1 \times 10^{-16}$ mol (1 to 0.1 fmol). The present inventors have achieved the sensitivity of ATP measurement of $1.0 \times 10^{-18}$ mol and attempted the measurement of one viable cell. However, when such ATP luminescence method is used in the pharmaceutical manufacturing field and particularly for the control of pharmaceutical water, microorganisms contained in extremely pure water, such as purified water and water for injection, or in other words, water, in which almost no nutrient is present, must be detected. In such a case, conventional techniques still have a problem that one viable cell cannot be measured.

PRIOR ART DOCUMENTS

Patent Documents

Patent Document 1: JP Patent No. 3547882
Patent Document 2: JP Patent Publication No. H11-253195 A (1999)
Patent Document 3: JP Patent Publication No. 2006-174751 A
Patent Document 4: JP Patent No. 3811616

Non-Patent Documents

Non-patent Document 1: Analytical Biochemistry Vol. 319, pp. 287-295, 2003

SUMMARY OF INVENTION

Problem to Be Solved by the Invention

Conventional ATP luminescence methods have problems that cells and particularly viable cells cannot be measured when the cell count in a sample is low or an ATP count in cells is low. On the other hand, it has been known that ATP in *E. coli, L. brevis, S. aureus*, or *B. subtilis* is increased by adding glucose (Patent Document 2). It has also been known that the addition of alanine induces the spore germination of *B. subtilis* (Patent Document 3). However, although Patent Document 2 discloses an ATP increase due to amino acids, it does not exemplify alanine and does not confirm the ATP-increasing effect of alanine. Moreover, Patent Document 3 discloses nothing about the ATP-increasing effect of glucose or alanine. Therefore, it has been extremely difficult to predict the ATP-increasing effect of alanine based on these two known examples.

As described above, these conventional techniques or combinations thereof are insufficient for simultaneously measuring a plurality of various types of cells including bacteria and fungi, sporulating (endospore-forming and spore-forming), nonsporulating, aerobic and anaerobic, and gram-negative and gram-positive microorganisms by a single ATP luminescence method.

Hence, an object of the present invention is to provide a method and a means, by which multiple types of cells (particularly, viable cells) can be simultaneously measured with high sensitivity by an ATP luminescence method.

Means for Solving the Problem

As a result of intensive studies to address the above problems, the present inventors have found that in an ATP luminescence method, methanol contributes to an increase in ATP within viable cells (live cells), thereby obtaining a finding that multiple types of cells (particularly, viable cells) can be simultaneously measured with high sensitivity by the use of methanol before an ATP extraction step. Thus, the present inventors have completed the present invention. Specifically, the present invention relates to the following [1] to [15].

[1] A method for measuring cells in a sample, comprising:
a first step of adding methanol to a sample suspected of containing viable cells to increase ATP within viable cells;
a second step of extracting intracellular ATP; and
a third step of causing extracted ATP to emit luminescence.

[2] The method according to [1], wherein in the first step, a substance selected from a sugar and alanine is further added to the sample.

[3] The method according to [1] or [2], wherein in the first step, ATPase is simultaneously added.

[4] The method according to any one of [1] to [3], wherein after the first step, cells are captured by a filter via filtration with the filter, a solution containing methanol is removed, and then the second and the third steps are performed.

[5] The method according to any one of [1] to [3], wherein after filtration of the sample using a filter, the first step and the second step are performed on the filter, and then the third step for causing the extracted ATP sample collected from the filter to emit luminescence is performed.

[6] The method according to any one of [1] to [5], wherein the concentration of methanol is less than 50%.

[7] The method according to any one of [2] to [6], wherein the sugar is at least one sugar selected from the group consisting of glucose, fructose, and sucrose.

[8] The method according to any one of [2] to [7], wherein the final concentration of the sugar is 0.8 mM or less.

[9] The method according to any one of [2] to [8], wherein the final concentration of alanine is 0.5 mM or less.

[10] The method according to any one of [2] to [9], wherein the final concentration of methanol is 1%, the final concentration of the sugar is 0.1 mM, and the final concentration of alanine is 0.1 mM.

[11] The method according to any one of [1] to [10], wherein a microorganism of at least one genus selected from the group consisting of the genus *Bacillus*, the genus *Pseudomonas*, the genus *Methylobacterium*, the genus *Escherichia*, the genus *Staphylococcus*, the genus *Clostridium*, the genus *Candida*, and the genus *Aspergillus* is used as a positive control for assuring the measurement method.

[12] The method according to any one of [1] to [10], wherein at least one microbial species selected from the group consisting of *Bacillus subtilis, Pseudomonas aeruginosa, Pseudomonas fluorescence, Methylobacterium extorquens, Escherichia coli, Staphylococcus aureus, Clostridium sporogenes, Candida albicans*, and *Aspergillus niger* is used as a positive control for assuring the measurement method.

[13] A reagent for performing the method for measuring cells according to any one of [1] to [12], comprising methanol.

[14] The reagent according to [13], further comprising a sugar and alanine.

[15] The reagent according to [13] or [14], which is supplied together with at least one type of reagent selected from the group consisting of ATPase, an ATP extraction solution, and a luminescent reagent.

This description includes part or all of the contents as disclosed in the specification and/or drawings of Japanese Patent Application No. 2011-265728 which is a priority document of the present application.

Effect of the Invention

According to the present invention, a method and a reagent for simultaneously measuring multiple types of cells (particularly, viable cells) in a sample with high sensitivity based on an ATP luminescence method are provided. Through the use of the method and the reagent of the present invention, an intracellular ATP level of more than 1 amol/CFU can be measured by a single measurement method. This is possible for multiple types of cells including bacteria and fungi, and sporulating (endospore-forming and spore-forming), nonsporulating, aerobic and anaerobic, and gram-negative and gram-positive microorganisms. Even when a cell count in a sample is low or an ATP level in cells is low, cells can be detected and cell counts can be measured. The present invention is applicable to various fields such as the pharmaceutical manufacturing, cosmetics manufacturing, clinical medicine, and basic biochemical fields. The present invention is particularly effective for the detection of cells and microorganisms under an oligotrophic environment, such as for the control of pharmaceutical water.

DETAILED DESCRIPTION OF THE INVENTION

The present invention will be described in detail as follows.
The present invention relates to a method for measuring cells in a sample based on an ATP luminescence method. The ATP luminescence method 141 according to the present invention (FIG. 1), makes it possible to simultaneously measure multiple types of cells (for example, microorganisms) with high sensitivity by one ATP luminescence measurement. According to the present invention, methanol (and further glucose and alanine) and ATPase 145 are added to a sample 142 containing multiple types of cells before an intracellular ATP extraction step 144 in order to increase ATP within viable cells (intracellular ATP increase) 150 and to remove ATP outside of viable cells (extracellular ATP removal) 143. In a preferred embodiment of the present invention, the step 150 for "increasing ATP within viable cells" and the step 143 for "removing ATP outside of viable cells" may be performed simultaneously.

The present invention is characterized by the finding that methanol contributes to an increase in ATP within viable cells (living microorganisms or live cells). This is not disclosed in both Patent Document 2 and Patent Document 3, and has been uniquely discovered by the present inventors. A conventional technique uses methanol in the ATP luminescence method as a mode of use in the "intracellular ATP extraction" step 144. According to the conventional technique, methanol is used in an ATP extraction step, cell walls are disrupted to cause cell (microorganism) death, and then ATP is extracted from cells (Patent Document 4). On the other hand, the present invention is characterized by using methanol before the "intracellular ATP extraction" step 144, so as to increase the intracellular ATP level under conditions where cells are living. Therefore, the effect achieved by the present invention is completely different from that achieved by the conventional technique that involves the use of methanol in the ATP extraction step (for example, see Example 3).

Furthermore, methanol has the activity of enzyme denaturation by which a protein such as an enzyme is denatured. The present inventors have confirmed that methanol can be used at concentrations allowing ATPase activity to be retained and viable cells to survive (see Examples 1 and 2). As described above, methanol has the activity of enzyme denaturation. Hence, if necessary, methanol may be removed before the "intracellular ATP extraction" step 144, followed by luminescence measurement.

In the present invention, first of all, methanol (final methanol concentrations ranging from 0.01 (v/v) % to 30 (v/v) %), glucose, alanine, and ATPase 145 are brought into contact with a sample 142 containing ATP within multiple types of viable cells and dead cells and free ATP. The extracellular ATP removal step 143 (for removing ATP outside of viable cells) and the intracellular ATP increase step 150 (for increasing ATP within viable cells) may involve about 5 to 360 minutes of heating at 25° C. to 50° C. in order to increase ATP within viable cells and degrade ATP outside of viable cells. Subsequently, methanol, glucose, alanine, and ATPase may be removed by filtration (146) with a filter, if necessary. Cell walls may be disrupted to extract ATP from the cells (144), and then an ATP extraction solution 147 may be added to inactivate ATPase. The thus extracted ATP may be brought into contact with a luminescent reagent 148 to cause a luminescent reaction 149 to take place. The resulting luminescence level may be quantified, so that a viable cell count in the sample can be quantified.

Therefore, in the method for measuring cells in a sample according to the present invention,
the first step of adding methanol to a sample suspected of containing viable cells to increase ATP within viable cells,
the second step of extracting intracellular ATP, and
the third step of causing the extracted ATP to emit luminescence are performed.

A sample may not be particularly limited, as long as it is suspected of containing viable cells to be measured. A sample may be a liquid, solid, or gas sample, or a mixture thereof. A liquid sample can be used directly, or can be diluted with a solvent or concentrated and then used. A solid sample may be suspended in a solvent, homogenized with a pulverizer or the like, and then used, or it may be agitated with a solvent to obtain a supernatant and then the supernatant may be used. For example, a stick such as a cotton swab is wetted with sterilized water, a measurement site is swabbed therewith, the swab is rinsed in a solvent, and then the thus obtained liquid may be used as a sample. Examples of a solvent may include distilled water, saline, phosphate buffer, and Tris buffer. Moreover, a sample may be filtered with a filter and then the filter that has captured sample ingredients (cells) can also be used. Such filter may not be particularly limited, as long as it has a size that enables capturing of cells. Specific examples of sample may include any samples for food and drink manufacturing, clinical examination (e.g., urine, feces, and blood), pharmaceutical manufacturing, cosmetics manufacturing, waste water treatment, bacteria testing (e.g., sea water, river water, industrial water, and soil), antimicrobial testing, cleanliness testing, and others. Such sample can be appropriately prepared by a person skilled in the art using methods and means that have been conventionally used for the ATP luminescence method.

Cells to be measured in the present invention may not be particularly limited, as long as these cells contain ATP. An object of the present invention is to determine if a sample to be measured contains cells. However, cells contained therein may be unknown and identifying them may be difficult. Therefore, when the measurement method is used, such unknown sample may be desirably measured after confirming that the measurement method is normal. This is a concept referred to as accuracy control. It is general to assure a measurement method using a negative control and a positive control.

As a positive control, a microorganism of at least one genus selected from the group consisting of the genus *Bacillus*, the genus *Pseudomonas*, the genus *Methylobacterium*, the genus *Escherichia*, the genus *Staphylococcus*, the genus *Clostridium*, the genus *Candida*, and the genus *Aspergillus* may be preferably used. Specifically, for example, the following cells can be used as positive control cells, and measured according to the present invention:

bacteria: gram-positive bacteria, such as an aerobic sporulating bacterium, *Bacillus subtilis*, an aerobic bacterium, *Staphylococcus aureus*, an aerobic bacterium, *Listeria monocytogenes*, and an anaerobic sporulating bacterium, *Clostridium sporogenes*;

gram-negative bacteria, such as aerobic bacteria, *Pseudomonas aeruginosa, Pseudomonas fluorescence, Methylobacterium extorquens*, and *Escherichia coli*, anaerobic bacteria of the genus *Salmonella*, and the genus *Legionella*; and Fungi: yeast such as *Candida albicans*, and *Saccharomyces cerevisiae*; and *Aspergillus niger*.

Preferably, among 9 species of viable cells (*Bacillus subtilis, Pseudomonas aeruginosa, Pseudomonas fluorescence, Methylobacterium extorquens, Escherichia coli, Staphylococcus aureus, Clostridium sporogenes, Candida albicans*, and *Aspergillus niger*) specified by the Japanese Pharmacopoeia, positive controls including 2 or more species, more preferably 5 or more species, and most preferably all 9 species specified herein may be used.

In the first step, methanol may be added to a sample suspected of containing viable cells. The concentration of methanol to be added may be a final concentration of less than 50%, preferably ranges from 0.1% to 30%, more preferably ranges from 0.1% to 5%, and may be 1%, for example. In addition when a filter is used as a sample, the filter can be immersed in a methanol solution, or a methanol solution can be added dropwise or sprayed to the filter.

Substances selected from a sugar and alanine may further be preferably added to a sample. As a sugar, at least one sugar selected from the group consisting of glucose, fructose, and sucrose can be used. A sugar may be added so that the final concentration thereof is 0.8 mM or less, and preferably 0.1 mM or less. Alanine may be added so that the final concentration thereof is 0.5 mM or less and preferably 0.1 mM or less. In a preferred embodiment, the final concentration of methanol may be 1% and the final concentration of a sugar may be 0.1 mM, and the final concentration of alanine may be 0.1 mM.

Simultaneously with the first step, ATP outside of viable cells may be removed. Specifically, ATPase may be added simultaneously with methanol. ATPase has been known in the art. Known ATPases can be used independently or in combination under appropriate reaction conditions (time, temperature, and pH). Specific examples thereof may include ATPases described in Patent Document 1 (JP Patent No. 3547882) such as adenosine-phosphate deaminase, apyrase, alkaline phosphatase, acid phosphatase, hexokinase, and adenosine triphosphatase. Furthermore, kits for performing the ATP luminescence method are commercially available and ATPase included with such a kit can be used. In addition, when a filter is used as a sample, the filter can be immersed in an ATPase solution, or an ATPase solution can be added dropwise or sprayed to the filter.

Here, the term "simultaneously" means not only performing two steps simultaneously, but also performing two steps successively. For example, methanol (if necessary, a sugar and alanine in addition to methanol) is added to a sample, ATPase may be added to the sample simultaneously with or subsequent to the addition, to perform a reaction. Alternatively, methanol (if necessary, a sugar and alanine in addition to methanol) may be added to a sample simultaneously with or after the addition of ATPase to the sample and then a reaction is performed. Moreover, the first step of adding methanol is performed, methanol in a sample is removed from the sample, and then ATPase may be added. Alternatively, ATPase is added, the extracellular ATP removal step (for removing ATP outside of viable cells) is performed, ATPase in the sample is removed, and then methanol may be added. In view of convenience for procedures, methanol and ATPase may be sequentially added to a sample to perform a reaction, preferably.

A reaction of a sample with methanol and/or ATPase may be performed at 25° C. to 50° C., and preferably 30° C. to 45° C. for 1 minute or more, preferably 1 minute to 6 hours, and more preferably for 5 minutes to 2 hours, although these conditions may differ depending on the ATPase type to be used, the methanol concentration, the cell type to be measured, and other conditions.

After the intracellular ATP increase step (for increasing ATP within viable cells) (the first step), methanol may be preferably removed from the sample. For this purpose, for example, after the above step, cells in a sample may be captured by a filter via filtration with the filter, a methanol-containing solution may be removed, and then the second and the third steps may be preferably performed. Furthermore, after the extracellular ATP removal step (for removing ATP outside of viable cells), ATPase may be preferably removed or inactivated. ATPase can be removed by, for example, filtration with a filter or the addition of an agent for inhibiting ATPase.

As an ATP extraction solution described later, a solution having activity to inactivate ATPase may also be used.

As described above, after filtration of a sample with a filter, the first and the second steps can also be performed on the filter using the filter as a sample. In this case, a methanol-containing solution and ATPase can be conveniently removed by washing the filter with pure water or buffer.

In the second step, intracellular ATP can be extracted. As a technique for extracting intracellular ATP, a known technique for the ATP luminescence method, such as a technique that involves adding an ATP extraction solution to a sample and then extracting intracellular ATP to outside the cells can be used. An ATP extraction solution may not be limited, as long as it enables extraction of ATP from cells. An ATP extraction solution by which ATPase can be inactivated is also known. Such ATP extraction solution is known and commercially available. Examples thereof may include trichloroacetic acid (TCA), surfactants (e.g., benzalkonium chloride and benzethonium chloride), and lysozyme. Depending on the type of an ATP extraction solution to be used, the amount thereof to be added to a sample, reaction conditions, and others may be appropriately selected. In addition, when a filter is used as a sample, the filter can be immersed in an ATP extraction solution, or an ATP extraction solution can be added dropwise or sprayed to the filter.

In the third step, extracted ATP may be caused to emit luminescence. To cause extracted ATP to emit luminescence and measure luminescence, a method generally employed in the ATP luminescence method, such as a luciferin-luciferase luminescent reaction can be used. The luciferin-luciferase luminescent reaction may be performed by adding a luminescent reagent containing luciferin and luciferase to a sample. The luminescent reagent may react with extracted ATP, thereby generating luminescence. The luminescence level can be measured. A luminescent reagent may be naturally-occurring luciferase or mutant luciferase. Commercially available product can be used. When a filter is used as a sample, an extracted ATP sample may be collected from the filter, a luminescent reagent may be added to the extracted ATP sample, and then luminescence emission can be performed. Alternatively, the filter may be immersed in a luminescent reagent or a luminescent reagent may be added dropwise to the filter and then luminescence emission may be performed on the filter.

Luminescence can be measured by a luminescence measurement method known in the art using a luminometer, a luminescence plate reader, or the like, or by photocounting using a photomultiplier. By measuring luminescence level, cells in a sample can be measured. In addition, the term "measurement of (measuring) cells" in the present invention means that the presence of cells in a sample is detected, as well as the number of cells is measured. The method of the present invention makes it possible to measure cells, and particularly multiple types of cells (viable cells) in a sample with high sensitivity, to an intracellular ATP level of more than 1 amol/CFU, for example, by performing the method one time, for example.

The above-described method of the present invention can be conveniently performed using the reagent of the present invention. The reagent of the present invention is characterized by containing methanol. The reagent of the present invention may further contain a sugar (for example, at least one sugar selected from the group consisting of glucose, fructose, and sucrose), and alanine. The reagent of the present invention may be supplied with at least one type of reagent selected from the group consisting of ATPase, an ATP extraction solution, and a luminescent reagent. These reagents may be preferably packaged together. A form of such reagent may be any form such as a form of solution, a powdery form, or a granular form. Preferably, these ingredients may be contained in forms and at concentrations appropriate for performing the method of the present invention. Instructions for implementation of the method for measuring cells may also be included with the reagent of the present invention.

EXAMPLES

The specific examples of the embodiments of the present invention are explained with reference to drawings as follows. It should be noted that these examples are merely examples for realizing the present invention and are not intended to limit the present invention.

Reference Example 1

ATP-Increasing Effect of Glucose and Alanine on *Bacillus subtilis*

*B. subtilis* spores in a cell suspension were purchased from Eiken Chemical Co., Ltd., and then cultured with agitation for 3 days in water for injection at 37° C., thereby preparing a cell suspension for ATP luminescence measurement.

An *M. extorquens* cell suspension was prepared according to the following procedures. *M. extorquens* was cultured with agitation in 5 mL of SCD liquid medium (Nissui Pharmaceutical Co., Ltd.) for 72 hours at 25° C. The culture solution (medium) was dispensed into tubes, and then centrifuged for 10 minutes at 10000 rpm, so as to collect cells onto the tube bottoms. Supernatant was removed, and then water was added instead, to suspend cells. Centrifugation was performed again for 10 minutes at 10000 rpm, so as to collect cells onto the tube bottoms. This step was repeated 3 times, medium components were removed, and thus a cell suspension was prepared. Subsequently, the cells were cultured with agitation in water for injection for 3 days at 37° C., so that a cell suspension for ATP luminescence measurement was prepared.

To measure the microbial colony counts, each cell (microbial) sample was diluted in water, as needed, and then R2A agar medium was coated with the cell suspension, followed by culture at 25° C. The colony counts were measured 96 to 168 hours after the initiation of culture.

Reagents included in a Lucifer HS set (Kikkoman Biochemifa Company) were used as reagents for ATP luminescence measurement. In addition, the Lucifer HS set comprises an ATP elimination enzyme, an ATP extraction reagent, and a luminescent reagent included therewith.

The ATP-increasing/decreasing effect of glucose and alanine on *B. subtilis* and *M. extorquens* was assessed according to the following procedures. 10 μL of glucose (Wako Pure Chemical Industries, Ltd.), 10 μL of alanine (Wako Pure Chemical Industries, Ltd.), and 10 μL of ATPase were added to 50 μL of the *B. subtilis* cell suspension or 50 μL of the *M. extorquens* cell suspension. Finally, a phosphate buffer (pH 7.4) (Invitrogen) was added for adjustment to total 100 μL volume. The final concentrations of glucose and alanine, and ATPase were 100 mM and 50 mM, and 10 (v/v) %, respectively. Each mixture was heated at 37° C. for 30 minutes. In addition, in Comparative Example 1, the addition of glucose and alanine was excluded from protocols described in the instructions for the reagent set.

100 μL of an ATP extraction solution was added to 100 μL of the mixture after heating. 50 μL of each sample after ATP extraction was added to 50 µL of the luminescent reagent. The thus generated luminescence was measured.

Table 1 below shows the results.

TABLE 1

| Protocol | Intracellular ATP level of *Bacillus subtilis* (amol/CFU) (%) | Intracellular ATP level of *Methylobacterium extorquens* (amol/CFU) (%) |
| --- | --- | --- |
| Comparative Example 1 | 0.004 (100%) | 0.7 |
| Comparative Example 2 | 1.2 (30000%) | 0.2 |

As shown in Table 1, in the case of the method of Comparative Example 1, the intracellular ATP level of *B. subtilis* that had formed spores under oligotrophic conditions (water for injection) was as low as 0.004 amol/CFU. Detection of 1 CFU was extremely difficult with this method.

Hence, glucose and alanine known to accelerate spore germination were added (Comparative Example 2) at 100 mM glucose and 50 mM alanine according to the previous report (J Bacteriol Vol. 81, p. 204, 1961). As a result, the intracellular ATP level of *B. subtilis* significantly increased (30000%), reaching the level at which 1CFU detection is possible. On the other hand, when *Methylobacterium extorquens* that is used for the medium performance test specified by the Japanese Pharmacopoeia for the control of pharmaceutical water was measured with the same protocols, the intracellular ATP level of *M. extorquens* decreased to 30% of the result obtained by the conventional method (Comparative Example 1).

Therefore, *M. extorquens* could not be measured with high sensitivity under the conditions. Moreover, it was difficult to simultaneously measure *B. subtilis* and *M. extorquens* with high sensitivity by a single ATP luminescence method.

*M. extorquens* is a methanol assimilating bacterium. In examples described later, the ATP-increasing effect of methanol was examined.

Reference Example 2

Effect of Methanol on ATP Luminescent Reaction

For examination of the ATP-increasing effect of methanol in examples described later, first of all the effect of methanol on an ATP luminescent reaction was confirmed.

1 mL of an ATP solution ($2 \times 10^5$ amol ATP/mL, Kikkoman Biochemifa Company Lucifer ATP standard reagent set) was mixed with 10 µl to 5 mL of 100% methanol (Wako Pure Chemical Industries, Ltd.). Water (Invitrogen) was further added to each solution, and thus ATP/methanol solutions (10 mL each) with final methanol concentrations ranging from 0.1 to 50 (v/v) % were prepared (ATP concentration: $2 \times 10^4$ amol ATP/mL). Subsequently, 50 µL of the ATP/methanol solution and 50 µL of a luminescent reagent (Kikkoman Biochemifa Company, included with a Lucifer HS set) were mixed to cause a luminescent reaction to take place. The resulting luminescence levels were measured by photocounting using a photomultiplier.

For comparison, 1 mL of a methanol-free ATP solution ($2 \times 10^4$ amol ATP/mL) was prepared. Subsequently, 50 µL of an ATP solution and 50 µL of the luminescent reagent were mixed to cause a luminescent reaction to take place, and then the luminescence level was measured.

Table 2 shows the luminescence levels according to methanol concentrations, resulting from the ATP•luciferase•luciferin reaction. Table 2 shows the comparisons of luminescence levels among the ATP solutions (sample Nos. 2 to 5) containing 0.1 to 50 (v/v) % methanol and the methanol-free ATP solution (sample No. 1), which had been mixed with the luminescent reagent.

TABLE 2

| Sample No. | Sample (/50 µL) | Luminescence level (CPS) | Relative luminescence (%) |
| --- | --- | --- | --- |
| 1 | 1000 amol ATP | 11534 | 100 |
| 2 | 1000 amol ATP 0.1% Methanol | 12703 | 110 |
| 3 | 1000 amol ATP 1% Methanol | 10200 | 88 |
| 4 | 1000 amol ATP 10% Methanol | 3345 | 29 |
| 5 | 1000 amol ATP 50% Methanol | 13 | 0 |

The luminescence levels of the ATP solution (sample No. 2) containing 0.1 (v/v) % methanol, the ATP solution (sample No. 3) containing 1 (v/v) % methanol, and the methanol-free ATP solution (sample No. 1) were 12703 CPS (Count per second), 10200 CPS, and 11534 CPS, respectively. The resulting luminescence percentages ranged from 88% to 110%. On the other hand, the luminescence percentage of the ATP solution (sample No. 4) containing 10 (v/v) % methanol decreased to 29%. The ATP solution (sample No. 5) containing 50 (v/v) % methanol emitted almost no fluorescence.

As a result, the methanol concentration to be added during the ATP luminescent reaction•measurement step is desirably 1 (v/v) % or less.

Example 1

In this example, methanol concentrations, at which ATPase activity can be retained, were examined.

10 µL of an ATPase-containing ATP elimination solution (Kikkoman Biochemifa Company, ATP elimination reagent included with a Lucifer HS set) was mixed with 80 µL of methanol, the concentration of which had been adjusted. An ATP solution ($2 \times 10^6$ amol/10 µL) was added to the solution and then it was left to stand at 37° C. for 30 minutes. In addition, the final methanol concentrations were adjusted to 0.1 to 80 (v/v) %.

To measure the remaining ATP level after the addition of the above mixture to a luminescent reagent, the mixture was diluted in water to a methanol concentration of 0.1 (v/v) % or less, assuring that the methanol would not affect the ATP luminescent reaction (Reference Example 2, Table 2). Subsequently, 50 µL of the diluted solution ($1 \times 10^3$ amol ATP/50 µL) was added to 50 µL of the luminescent reagent, and then the luminescence level was measured. Furthermore, an ATP solution ($1 \times 10^3$ amol/50 µL) to which no ATPase had been added was prepared. The luminescence level according to the ATP solution was also measured. The luminescence level of the ATPase-free ATP solution was considered almost the same as that of an ATP solution to which ATP had been added after the loss of ATPase activity. Hence, the luminescence level was defined as the residual ATPase activity of 0%.

Figure 2:
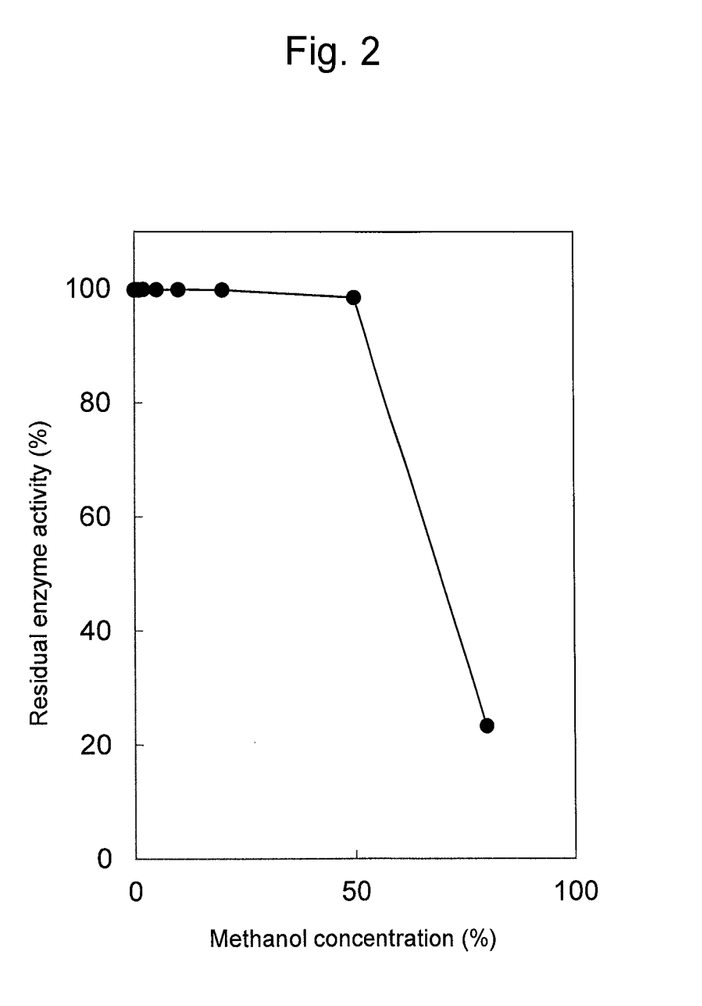
FIG. 2 shows residual ATPase activity according to methanol concentrations.

FIG. 2 shows the residual ATPase activity according to methanol concentrations. No ATP luminescent reaction was measured from the mixture of ATPase and the ATP solution in the presence of 0 to 50 (v/v) % methanol. This indicates that ATPase retained the activity at methanol concentrations ranging from 0 to 50 (v/v) % and degraded ATP added. On the other hand, ATPase activity began decreasing when the methanol concentration exceeded 50 (v/v) %. The enzyme activity decreased to 20% when the methanol concentration was 80 (v/v) %.

As a result, it was revealed that when the methanol concentration is 50 (v/v) % or less, ATP outside of viable cells can be degraded without inactivating ATPase.

Example 2

In this example, since methanol originally has an antiseptic effect, the effect of methanol concentrations on bacteria to be assessed was examined.

10 μL of a cell suspension and 90 μL of methanol, the concentration of which had been adjusted, were mixed, thereby preparing 100 μL of a cell/methanol suspension. The final methanol concentrations ranged from 0 to 80 (v/v) %. As microorganisms (cells), *Bacillus subtilis* (bacterium, spores, ATCC 6633), *Staphylococcus aureus* (bacterium, aerobic, ATCC 6538), and *Candida albicans* (fungus, yeast, ATCC 10231) were used. Each cell suspension was mixed with methanol and then the mixture was left to stand for 1 minute. In the case of bacteria, the mixture was applied and spread over R2A medium (Nissui Pharmaceutical Co., Ltd.) and then cultured at 25° C. for 7 days. In the case of fungi, the mixture was applied and spread over PDA medium (Nissui Pharmaceutical Co., Ltd.) and then cultured at 25° C. for 5 days. After culture, the colony count was then measured according to each methanol concentration. The colony count in the case of 0% methanol was designated as 100% cell viability. Cell viability according to each methanol concentration was examined.

Figure 3:
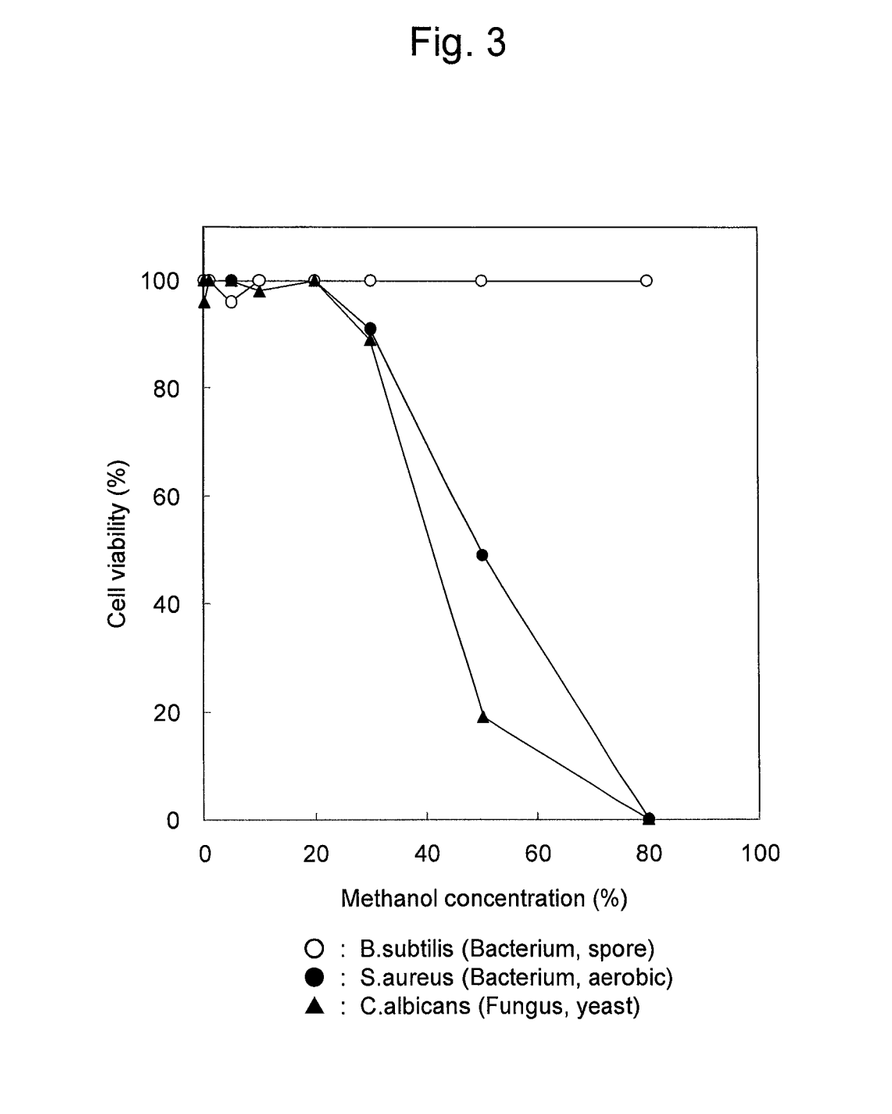
FIG. 3 shows the viability of *B. subtilis, S. aureus*, and *C. albicans* according to methanol concentrations.

FIG. 3 shows the cell viability according to each methanol concentration. *B. subtilis* exhibited 100% cell viability even when exposed to 80 (v/v) % methanol. On the other hand, *S. aureus* and *C. albicans* exhibited 90% or more cell viability when exposed to a maximum of 30 (v/v) % methanol.

The results indicate that a maximum 30 (v/v) % methanol concentration maintains the homeostatic activity required for all three targeted microbes, *B. subtilis*, *S. aureus*, and *C. albicans* to keep their intracellular biological activity.

Example 3

In this example, the ATP-increasing effect of methanol on *M. extorquens* was examined.

An *M. extorquens* cell suspension was prepared according to the following procedures. *M. extorquens* was cultured with agitation in 5 mL of SCD liquid medium (Nissui Pharmaceutical Co., Ltd.) for 72 hours at 25° C. The culture solution (medium) was dispensed into tubes, and then centrifuged for 10 minutes at 10000 rpm, so as to collect cells onto the tube bottoms. Supernatant was removed, and then water was added instead, to suspend cells. Centrifugation was performed again for 10 minutes at 10000 rpm, so as to collect cells onto the tube bottoms. This step was repeated 3 times, medium components were removed, and thus a cell suspension was prepared. Subsequently, the cells were cultured with agitation in water for injection for 3 days at 37° C., so that a cell suspension for ATP luminescence measurement was prepared.

To measure the microbial colony counts, each cell (microbial) sample was diluted in water, as needed, and then R2A agar medium was coated with the cell suspension, followed by culture at 25° C. The colony counts were measured 96 to 168 hours after the initiation of culture.

Hereinafter, a first embodiment using the thus prepared cell suspension is described. The first embodiment is luminescence measurement that involves only the mixing of various reagents.

10 μL each of glucose (Wako Pure Chemical Industries, Ltd.), alanine (Wako Pure Chemical Industries, Ltd.), ATPase, 10% methanol, and a phosphate buffer (pH 7.4) (Invitrogen) were added to 50 μL of the *M. extorquens* cell suspension, thereby preparing a total of 100 μL of a mixture. When glucose, alanine, and methanol were not added, the solution was adjusted to a total 100 μL volume with a phosphate buffer (Table 3, sample Nos. 1 to 5). The mixture was heated at 37° C. for 30 minutes. In the extracellular ATP removal•intracellular ATP increase step (for removing ATP outside of viable cells and increasing ATP within viable cells), 100 μL of an ATP extraction solution was added to 100 μL of the mixture (Table 3, sample Nos. 1 to 4). For comparison of the ATP extraction efficiency of methanol, in the ATP extraction step, 100 μL, of the mixture was mixed with 100 μL of a 1% methanol-containing ATP extraction solution (Table 3, sample No. 5). After ATP extraction, 50 μL of the sample was added to 50 μL of the luminescent reagent, and then the thus generated luminescence was measured.

Hereinafter, a second embodiment using the thus prepared cell suspensions is described. The second embodiment differs from the first embodiment in that filtration was employed in the second embodiment for collecting cells and removing methanol.

50 μL of the *M. extorquens* cell suspension was subjected to centrifugal filtration (1 min, 2000 rpm) using Ultrafree-MC (Millipore, pore size of 0.45 μm, membrane filter made of polyvinylidene fluoride), thereby collecting cells on the filter. 10 μL each of glucose, alanine, ATPase, and 10% methanol and 70 μL of a phosphate buffer (pH7.4) were added onto the filter, thereby preparing a total of 100 μL of a mixture. The final concentrations of glucose and alanine were each 0.1 mM, and the final concentrations of ATPase and methanol were 10% and 1%, respectively (Table 3, sample No. 6). Each mixture on the filter was heated at 37° C. for 30 minutes. After heating, to remove methanol-containing mixtures, all mixtures were subjected to centrifugal filtration (1 min, 2000 rpm) using Ultrafree-MC, and then mixtures as filtrates were discarded. Subsequently, 200 μL of water was added onto the filter, and filtrated to wash the filter. In addition, washing was repeated 5 times. After washing, 100 μL of an ATP extraction solution was added onto the filter, the filter was left to stand for 5 minutes, and then centrifugal filtration (2000 rpm, 1 min) was performed to recover the filtrate. After each ATP extraction, 50 μl of sample was added to 50 μL of a luminescent reagent. The thus generated luminescence was measured.

Table 3 shows the intracellular ATP level per CFU (amol/CFU) of *M. extorquens*, as measured by the intracellular ATP luminescence method.

TABLE 3

| Sample No. | Extracellular ATP removal intracellular ATP increase step | Filtration | ATP extraction step | ATP level (amol/CFU)(%) |
|---|---|---|---|---|
| 1 | 10% ATPase | No | ATP extraction solution | 0.7 (100%) |
| 2 | 10% ATPase 100 mM Glucose 50 mM Alanine | No | ATP extraction solution | 0.2 (29%) |

TABLE 3-continued

| Sample No. | Extracellular ATP removal intracellular ATP increase step | Filtration | ATP extraction step | ATP level (amol/CFU)(%) |
|---|---|---|---|---|
| 3 | 10% ATPase 0.1 mM Glucose 0.1 mM Alanine | No | ATP extraction solution | 0.9 (129%) |
| 4 | 10% ATPase 1% Methanol 0.1 mM Glucose 0.1 mM Alanine | No | ATP extraction solution | 1.2 (171%) |
| 5 | 10% ATPase 0.1 mM Glucose 0.1 mM Alanine | No | ATP extraction solution 1% Methanol | 0.8 (114%) |
| 6 | 10% ATPase 1% Methanol 0.1 mM Glucose 0.1 mM Alanine | Yes | ATP extraction solution | 1.2 (171%) |

The results of sample No. 1 and sample No. 2 were the same as those in Example 1. As shown in the result of sample No. 2, *M. extorquens* inhibited by alanine and glucose was observed. Hence, the concentrations of alanine and glucose were decreased to reduce the inhibition. In the case of sample No. 3 for which 0.1 mM alanine and 0.1 mM glucose had been used, the ATP level of *M. extorquens* increased to 0.9 amol/CFU. Thus, the concentrations by which inhibition can be avoided and the ATP level can be increased by about 30% compared with the conventional method (Comparative Example 1 of Reference Example 1) were discovered.

Furthermore, to examine the ATP-increasing effect of methanol, methanol was added to a final concentration of 1 (v/v) %. As in the case of sample No. 4, the ATP level increased to 1.2 amol/CFU. Specifically, the ATP level could be increased by about 70% compared with that of the conventional method (Comparative Example 1 of Reference Example 1).

To confirm if the effect of the addition of methanol was the effect that had increased the intracellular ATP level, or the effect of methanol on ATP extraction as disclosed in Patent Document 4 (JP Patent No. 3811616), the effect of the addition of methanol was verified by adding 1 (v/v) % methanol not in the "extracellular ATP removal•intracellular ATP increase step", but in the "ATP extraction" step as in the case of sample No. 5. As a result, the ATP level in the case of sample No. 5 was 0.8 amol/CFU that was at the same level as that in the case of sample No. 3. It was thus confirmed that 1 (v/v) % methanol has no effect on ATP extraction.

Moreover, as in the conditions for sample No. 6, 1% methanol was added in the "extracellular ATP removal•intracellular ATP increase step", and then filtration and washing were performed to prevent methanol, glucose, and alanine from remaining in the "ATP extraction" step. Even in this case, the ATP level was maintained at 1.2 amol/CFU. Hence, it was revealed that the addition of 1 (v/v) % methanol in the "extracellular ATP removal•intracellular ATP increase step" has an effect of increasing the intracellular ATP level in viable cells.

Example 4

In this example, the relationship between the ATP level in *M. extorquens* and the amounts of glucose and alanine was examined.

An *M. extorquens* cell suspension was prepared according to the following procedures. *M. extorquens* was cultured with agitation in 5 mL of SCD liquid medium (Nissui Pharmaceutical Co., Ltd.) for 72 hours at 25° C. The culture solution (medium) was dispensed into tubes, and then centrifuged for 10 minutes at 10000 rpm, so as to collect cells onto the tube bottoms. Supernatant was removed, and then water was added instead, to suspend cells. Centrifugation was performed again for 10 minutes at 10000 rpm, so as to collect cells onto the tube bottoms. This step was repeated 3 times, medium components were removed, and thus a cell suspension was prepared. Subsequently, the cells were cultured with agitation in water for injection for 3 days at 37° C., so that a cell suspension for ATP luminescence measurement was prepared.

To measure the microbial colony counts, each cell (microbial) sample was diluted in water, as needed, and then R2A agar medium was coated with the cell suspension, followed by culture at 25° C. The colony counts were measured 96 to 168 hours after the initiation of culture.

10 μL each of glucose, alanine, ATPase, and if necessary, 10 (v/v) % methanol were added to 50 μL of the *M. extorquens* cell suspension. Finally, a phosphate buffer (pH 7.4) (Invitrogen) was added for adjustment to a total 100 μL volume. The final concentrations of glucose and alanine ranged from 0.1 mM to 100 mM, and the final concentrations of ATPase and methanol were 10 (v/v) % and 1 (v/v) %, respectively. Each mixture was heated at 37° C. for 30 minutes. 100 μL of an ATP extraction solution was added to 100 μL of the heated mixture, and then 50 μL of sample after ATP extraction was added to 50 μL of a luminescent reagent. The thus generated luminescence was measured.

Figure 4:
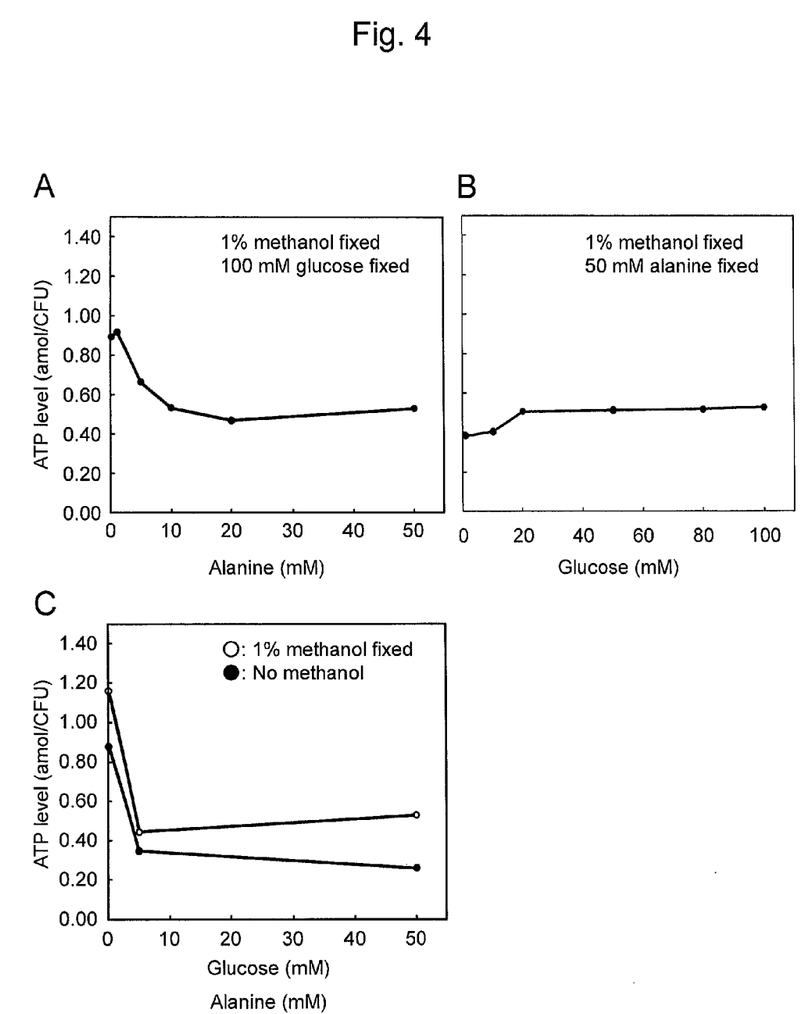
FIG. 4 shows the effects of various additives on the intracellular ATP levels of *M. extorquens*.

FIG. 4A shows the intracellular ATP level of *M. extorquens* per CFU (amol/CFU) when the alanine concentration was varied from 0.1 mM to 50 mM in the presence of 1 (v/v) % methanol and 100 mM glucose. The intracellular ATP level of *M. extorquens* increased when the alanine concentration was 10 mM or less, but was 0.9 amol/CFU when the same was 1 mM or less.

FIG. 4B shows the intracellular ATP level per CFU (amol/CFU) when the glucose concentration was varied from 0.1 mM to 100 mM in the presence of 1 (v/v) % methanol and 50 mM alanine. The intracellular ATP level of about 0.5 amol/CFU remained unchanged even when the glucose concentration was varied.

FIG. 4C shows the intracellular ATP levels per CFU when the concentrations of glucose and alanine were varied simultaneously from 0.1 mM, 5 mM, and then to 50 mM in the presence or the absence of methanol. The intracellular ATP level increased rapidly when each concentration was 5 mM or less in the absence of methanol, such that it was 0.9 amol/CFU when the concentration was 0.1 mM. The result was the same as that of a combination of 0.1 mM alanine, 100 mM glucose, and 1% methanol (FIG. 4A). However, when 1% methanol was added to 0.1 mM alanine and 0.1 mM glucose, the intracellular ATP level increased to 1.2 amol/CFU. This indicates that when the concentrations of alanine and glucose are each less than 5 mM and methanol is further added, the ATP level increases.

Patent document 3 (JP Patent Publication No. 2006-174751A) discloses that glucose and alanine have an effect of accelerating the germination of sporulating bacteria, but does not disclose the ATP-increasing effect. Moreover, the presence of the optimal concentration ranges of glucose, alanine, and a combination thereof for the ATP-increasing effect, was discovered by the present inventors as shown in the results in FIG. 4.

Example 5

In this example, the effect of increasing or decreasing intracellular ATP levels according to methanol concentrations was examined.

An *M. extorquens* cell suspension was prepared according to the following procedures. *M. extorquens* was cultured with agitation in 5 mL of SCD liquid medium (Nissui Pharmaceutical Co., Ltd.) for 72 hours at 25° C. The culture solution (medium) was dispensed into tubes, and then centrifuged for 10 minutes at 10000 rpm, so as to collect cells onto the tube bottoms. Supernatant was removed, and then water was added instead, to suspend cells. Centrifugation was performed again for 10 minutes at 10000 rpm, so as to collect cells onto the tube bottoms. This step was repeated 3 times, medium components were removed, and thus a cell suspension was prepared. Subsequently, the cells were cultured with agitation in water for injection for 3 days at 37° C., so that a cell suspension for ATP luminescence measurement was prepared.

To measure the microbial colony counts, each cell (microbial) sample was diluted in water, as needed, and then R2A agar medium was coated with the cell suspension, followed by culture at 25° C. The colony counts were measured 96 to 168 hours after the initiation of culture.

10 µL each of glucose, alanine, ATPase, and methanol were added to 50 µL of the *M. extorquens* cell suspension. Finally, a phosphate buffer (pH 7.4) (Invitrogen) was added for adjustment to a total 100 µL volume. The final concentrations of glucose and alanine were each 0.1 mM, the final ATPase concentration was 10 (v/v) %, and the final methanol concentrations ranged from 0% to 80%. Each mixture was heated at 37° C. for 30 minutes. After heating, to remove methanol-containing mixtures, all mixtures were subjected to centrifugal filtration (1 min, 2000 rpm) using Ultrafree-MC, and then mixtures as filtrates were discarded. Subsequently, 200 µL of water was added onto the filter and filtrated to wash the filter. In addition, washing was repeated 5 times. After washing, 100 µL of an ATP extraction solution was added onto the filter, the filter was left to stand for 5 minutes, and then centrifugal filtration (2000 rpm, 1 min) was performed to recover the filtrate. After each ATP extraction, 50 µl of sample was added to 50 µL of a luminescent reagent. The thus generated luminescence was measured.

Figure 5:
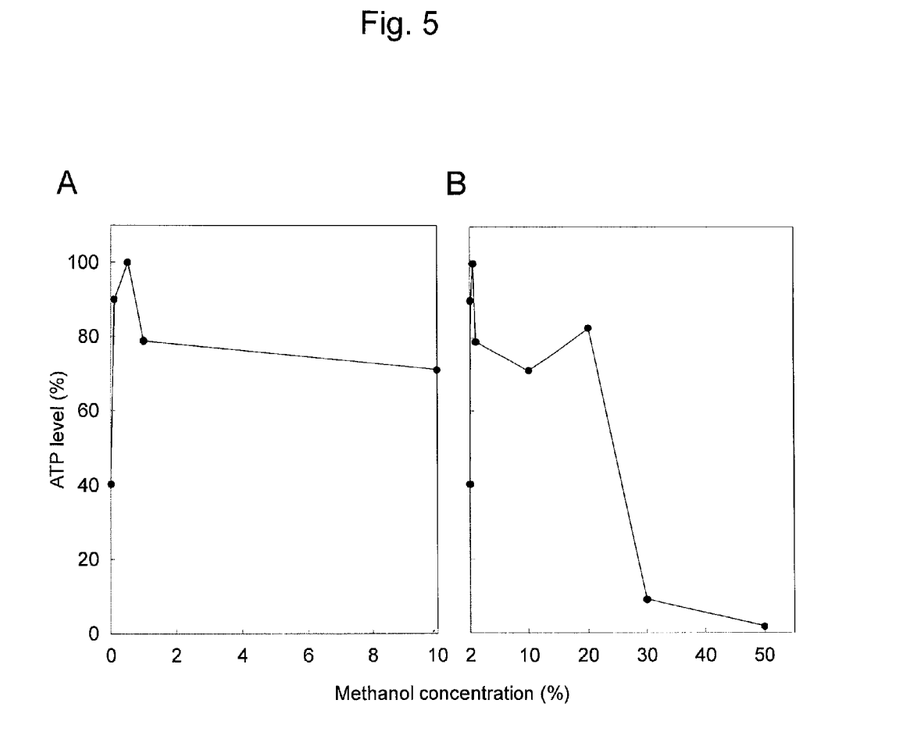
FIG. 5 shows the intracellular ATP levels of *M. extorquens* according to methanol concentrations.

FIG. 5A shows the intracellular ATP levels of *M. extorquens* according to methanol concentrations ranging from 0% to 10%. The intracellular ATP level of *M. extorquens* was the highest (1.5 amol/CFU) at the methanol concentration of 0.5%, and decreased by 60% (0.7 amol/CFU) when the methanol concentration was 0%. When the methanol concentrations ranged from 0.1% to 20%, the intracellular ATP level was 1.1 amol/CFU corresponding to 70% or more of the maximum (FIGS. 5A and B). On the other hand, when the methanol concentration was 30% or more, the intracellular ATP level decreased by 90% (0.15 amol/CFU) (FIG. 5B).

Example 6

According to the Japanese Pharmacopoeia, a total of 9 species below are specified as microorganisms to be used for a medium test in order to confirm if a medium is appropriate for the "control of pharmaceutical water" or "sterility test": an aerobic sporulating bacterium, (gram-positive) *Bacillus subtilis* (ATCC 6633), an aerobic bacterium, (gram-negative) *Pseudomonas aeruginosa* (NBRC 13275), an aerobic bacterium, (gram-negative) *Pseudomonas fluorescence* (NBRC 15842), an aerobic bacterium, (gram-negative) *Methylobacterium extorquens* (NBRC 15911), an aerobic bacterium (gram-negative) *Escherichia coli* (ATCC 11775), an aerobic bacterium, (gram-positive) *Staphylococcus aureus* (ATCC 6538), an anaerobic sporulating bacterium, (gram-positive) *Clostridium sporogenes* (ATCC 11437), a fungus, (yeast) *Candida albicans* (ATCC 10231), and a fungus (mold•spore) *Aspergillus niger* (ATCC 16404). Here, the term "ATCC" represents a catalog number of the American Type Culture Collection, and the term "NBRC" represents an accession number of the NITE Biological Resource Center.

In this example, intracellular ATP was measured for the above 9 species of biological indicators specified in the Japanese Pharmacopoeia.

The cell suspensions of nonsporulating bacteria (*P. aeruginosa, P. fluorescence, M. extorquens, S. aureus, E. coli*, and *C. albicans*) were prepared according to the following procedures. Each bacterium was added to 5 mL of SCD liquid medium, and then cultured with agitation for 48 hours. The temperatures for culture were, on the basis of the Japanese Pharmacopoeia, 37° C. for *S. aureus* and *E. coli*, and 25° C. for *P. fluorescence, P. aeruginosa, M. extorquens*, and *C. albicans*. The culture solutions after culture were dispensed into tubes, and then centrifuged at 10000 rpm for 10 minutes, thereby collecting cells onto the tube bottoms. For all cells, Supernatant containing each component were removed and water was added instead, to suspend cells. Centrifugation was performed at 10000 rpm for 10 minutes so as to collect cells again onto the tube bottoms. This step was repeated 3 times, so as to remove and replace each component with water. Subsequently, cells were cultured with agitation in water for injection for 3 days at 37° C., thereby preparing cell suspensions for ATP luminescence measurement.

To measure the colony count of each species, if necessary, each cell (microbial) sample was diluted in water, and then R2A agar medium was coated with the *M. extorquens* suspension, followed by culture at 25° C. The colony count was measured 96 hours to 168 hours after the initiation of culture. Standard agar media were coated with bacterial suspensions of *B. subtilis, P. aeruginosa, P. fluorescence, E. coli, S. aureus*, and *C. sporogenes*, followed by culture at 25° C. Colony counts were measured at 96 hours to 168 hours after the initiation of culture. PDA media were coated with the fungal suspensions of *C. albicans* and *A. niger*, fungi on each medium were cultured at 20° C. and colony counts were measured at 120 hours after the initiation of culture.

10 µL each of glucose, alanine, ATPase, and 10% methanol were added, if necessary, to 50 µL of the cell suspension of each species. A phosphate buffer (pH 7.4) was then added to prepare a total of 100 µL of a mixture. The final concentrations of glucose and alanine were each 0.1 mM, and the final concentrations of ATPase and methanol were 10% and 1%, respectively. Each mixture was heated at 37° C. for 30 minutes. After heating, 100 µL of an ATP extraction solution was added to 100 μL of the mixture. After each ATP extraction, 50 μL of sample was mixed with 50 μL of a luminescent reagent. The thus generated luminescence was measured.

Table 4 shows the ATP increasing effect of methanol, glucose, and alanine on the above-specified 9 species in the ATP luminescence method.

higher that of the conventional method, the intracellular ATP level of *C. sporogenes* was nearly 4 times higher than that of the conventional method, and the intracellular ATP levels of *E. coli* and *B. subtilis* were unchanged with methanol exposure compared to that of the conventional method. On the other hand, the intracellular ATP levels of *A. niger* and *C.*

TABLE 4

| | Intracellular ATP level (amol/CFU) % compared with Comparative Example 1 | | | |
|---|---|---|---|---|
| Microbial species | Comparative Example 1 | Comparative Example 2 50 mM Alanine 100 mM Glucose 10% ATP elimination solution | Example 6-1 0.1 mM Alanine 0.1 mM Glucose 10% ATP elimination solution | Example 6-2 0.1 mM Alanine 0.1 mM Glucose 1% Methanol 10% ATP elimination solution |
| *Bacillus subtilis* (Aerobic bacterium, Gram-positive, Spore) | 0.004 (100%) | 1.2 (30000%) | 2.1 (52500%) | 2.1 (52500%) |
| *Methylobacterium extorquens* (Aerobic bacterium, Gram-negative) | 0.7 (100%) | 0.2 (29%) | 0.9 (129%) | 1.2 (171%) |
| *Staphylococcus aureus* (Aerobic bacterium, Gram-positive) | 2.3 (100%) | 1.7 (74%) | 2.9 (126%) | 6.3 (274%) |
| *Pseudomonas fluorescens* (Aerobic bacterium, Gram-negative) | 1.8 (100%) | 2.3 (128%) | 5.4 (300%) | 4.6 (256%) |
| *Pseudomonas aeruginosa* (Aerobic bacterium, Gram-negative) | 1.9 (100%) | 2.7 (142%) | 5.3 (279%) | 5.0 (263%) |
| *Escherichia coli* (Aerobic bacterium, Gram-negative) | 4.5 (100%) | 3.0 (67%) | 3.8 (84%) | 4.8 (107%) |
| *Clostridium sporogenes* (Anaerobic bacterium, Spore) | 6.1 (100%) | 6.1 (100%) | 18.1 (297%) | 23.3 (382%) |
| *Aspergillus niger* (Fungus, Mold, Spore) | 24 (100%) | 10.3 (43%) | 6.1 (25%) | 8.2 (34%) |
| *Candida albicans* (Fungus, Yeast) | 132 (100%) | 62.7 (48%) | 98.3 (74%) | 110.1 (83%) |

As described in Reference Example 1 for *B. subtilis*, the detection of 1 CFU was difficult in Comparative Example 1. The intracellular ATP level of each microbial species under conditions of 100 mM glucose and 50 mM alanine having the ATP-increasing effect was examined (Comparative Example 2). The ATP-increasing effect was observed dramatically on *B. subtilis*. Moreover, the ATP-increasing effect equivalent to or the effect 1.5 times higher was observed on *P. fluorescens*, *P. aeruginosa*, and *C. sporogenes*. The inhibition of the ATP-increasing effect was observed on other microorganisms.

Accordingly, as a result of decreasing the concentrations of glucose and alanine to 0.1 mM (Example 6-1), the ATP-increasing effect was observed on *M. extorquens, S. aureus, P. fluorescens, P. aeruginosa*, and *C. sporogenes* having relatively low intracellular ATP levels. The intracellular ATP level of *B. subtilis* was maintained. Moreover, regarding *A. niger* and *C. albicans* having high intracellular ATP levels, whereas recovery from the conditions due to the inhibition of glucose and alanine was not observed, the ATP levels remained sufficient for 1 CFU detection.

Furthermore, when methanol was added to a final concentration of 1 (v/v) % (Example 6-2), the intracellular ATP level of *M. extorquens* was 1.7 times higher than that of the conventional method, the intracellular ATP levels of *S. aureus, P. fluorescens*, and *P. aeruginosa* were each nearly 3 times *albicans* were over 30% and 80% of that of the conventional method, respectively. Because of their high absolute ATP levels, it was revealed that these intracellular ATP levels were sufficient for detection of 1 CFU. As described above, the surprising effect of methanol, such that methanol has the ATP-increasing effect not only on a methanol-assimilating bacterium, *M. extorquens*, but also on many other microbial species, was discovered.

It was also demonstrated by these results that the above 9 microbial species can be detected according to this measurement method. It was thus confirmed that these microbial species can be used as positive controls for accuracy control. Therefore, at least one microbial species selected from the group of these 9 species can be used as a positive control.

Measurement of cell counts (particularly, viable cell counts) by a conventional method requires a plurality of media, culture temperatures, and culture time. Simultaneous measurements have been difficult or unknown. The present invention makes it possible to simultaneously detect bacteria and fungi, multiple types of microorganisms including sporulating (endospore-forming and spore-forming), nonsporulating, aerobic and anaerobic, gram-negative and gram-positive microorganisms, and cells with extremely low intracellular ATP levels, with high sensitivity.

In addition, the present invention is not limited to the above examples and can include various modifications and changes.

For example, the above examples are described in detail to provide a simple explanation of the present invention. The present invention is not always limited to an invention that comprises all of the elements explained herein. Furthermore, a portion of the element(s) of an example can be substituted with the element(s) of another example, and the element(s) of one example can also be added to the element(s) of another example. Moreover, another element(s) can be added to, deleted from, or substituted with a portion of the element(s) of any example.

DESCRIPTION OF SYMBOLS

101 Flow of ATP luminescence measurement step according to conventional method
102 Sample
103 Extracellular ATP removal step (step for removing ATP outside of viable cells)
104 Intracellular ATP extraction step
105 ATP luminescent reaction•measurement step
106 ATPase
107 ATP extraction solution
108 Luminescent reagent
121 Changes in the states of ATP within viable cells, ATP within dead cells, free ATP, and ATPase in each step of ATP luminescence method
122 Viable cells
123 ATP within dead cells•free ATP
124 ATPase
125 Presence of ATPase activity
126 Degradation of ATP outside of viable cells
127 Survival of viable cells
128 Intracellular ATP extraction
129 No ATPase activity
130 ATP luminescent reaction
141 Flow of ATP luminescence measurement steps according to the present invention
142 Sample containing multiple types of cells
143 Extracellular ATP removal (removal of ATP outside of viable cells)
144 Intracellular ATP extraction step
145 ATPase.methanol.glucose.alanine
146 Filtration step
147 ATP extraction solution
148 Luminescent reagent
149 ATP luminescent reaction•measurement step
150 Intracellular ATP increase step (step for increasing ATP within viable cells)

All publications, patents, and patent applications cited herein are incorporated herein by reference in their entirety.

The invention claimed is:

1. A method for measuring cells in a sample, comprising:
a first step comprising adding a solution comprising 0.1% to 20% methanol to a sample suspected of containing viable cells to increase ATP within the viable cells and adding an enzyme to remove ATP outside of the viable cells:
a second step of extracting intracellular ATP following the first step of increasing intracellular ATP and removing extracellular ATP; and
a third step of causing the extracted intracellular ATP to emit luminescence and measuring a luminescence level thereof.

2. The method according to claim 1, wherein in the first step, a substance selected from a sugar and alanine is further added to the sample.

3. The method according to claim 2, wherein the sugar is at least one sugar selected from the group consisting of glucose, fructose, and sucrose.

4. The method according to claim 2, wherein the final concentration of the sugar is 0.8 mM or less.

5. The method according to claim 2, wherein the final concentration of alanine is 0.5 mM or less.

6. The method according to claim 2, wherein the final concentration of methanol is 1%, the final concentration of the sugar is 0.1 mM, and the final concentration of alanine is 0.1 mM.

7. The method according to claim 1, wherein in the first step, the methanol and enzyme are added simultaneously and the enzyme is ATPase.

8. The method according to claim 1, wherein after the first step, cells are captured by a filter via filtration with the filter, a solution containing methanol is removed, and then the second and the third steps are performed.

9. The method according to claim 1, wherein suspected of containing viable cells has been prepared by filtering a solution suspected of containing viable cells and the first step and the second step are performed on the filter used.

10. The method according to claim 1, wherein a microorganism of at least one genus selected from the group consisting of the genus *Bacillus*, the genus *Pseudomonas*, the genus *Methylobacterium*, the genus *Escherichia*, the genus *Staphylococcus*, the genus *Clostridium*, the genus *Candida*, and the genus *Aspergillus* is used as a positive control.

11. The method according to claim 1, wherein at least one microbial species selected from the group consisting of *Bacillus subtilis, Pseudomonas aeruginosa, Pseudomonas fluorescence, Methylobacterium extorquens, Escherichia coli, Staphylococcus aureus, Clostridium sporogenes, Candida albicans*, and *Aspergillus niger* is used as a positive control.

12. The method according to claim 1, wherein in the first step, the solution comprising methanol is removed prior to the second step.

* * * * *